United States Patent
Prawer et al.

(10) Patent No.: US 10,543,372 B2
(45) Date of Patent: Jan. 28, 2020

(54) METHOD OF FORMING AN ENCLOSURE

(71) Applicants: THE UNIVERSITY OF MELBOURNE, Melbourne, Victoria (AU); NATIONAL ICT AUSTRALIA LIMITED, Eveleigh, New South Wales (AU)

(72) Inventors: Steven Prawer, Melbourne (AU); Kumaravelu Ganesan, Melbourne (AU); David Garrett, Melbourne (AU); Nicholas Apollo, Melbourne (AU); Alastair Stacey, Melbourne (AU); Mathilde Escudie, Melbourne (AU); Hamish Meffin, Eveleigh (AU); Samantha Lichter, Eveleigh (AU)

(73) Assignees: The University of Melbourne, Melbourne, Victoria (AU); National ICT Australia Limtied, Eveleigh, New South Wales (AU)

( * ) Notice: Subject to any disclaimer, the term of this patent is extended or adjusted under 35 U.S.C. 154(b) by 111 days.

(21) Appl. No.: 15/522,632

(22) PCT Filed: Oct. 28, 2015

(86) PCT No.: PCT/AU2015/000646
§ 371 (c)(1),
(2) Date: Apr. 27, 2017

(87) PCT Pub. No.: WO2016/065399
PCT Pub. Date: May 6, 2016

(65) Prior Publication Data
US 2017/0312528 A1    Nov. 2, 2017

(30) Foreign Application Priority Data
Oct. 28, 2014    (AU) .................................. 2014904311

(51) Int. Cl.
*A61N 1/375* (2006.01)
*B23K 35/30* (2006.01)
(Continued)

(52) U.S. Cl.
CPC ............ *A61N 1/375* (2013.01); *B23K 1/0016* (2013.01); *B23K 1/19* (2013.01); *B23K 26/21* (2015.10);
(Continued)

(58) Field of Classification Search
CPC combination set(s) only.
See application file for complete search history.

(56) References Cited

U.S. PATENT DOCUMENTS

| | | |
|---|---|---|
| 2004/0155096 A1 | 8/2004 | Zimmerman et al. |
| 2013/0022836 A1 | 1/2013 | Easley et al. |

(Continued)

FOREIGN PATENT DOCUMENTS

| | | |
|---|---|---|
| WO | 0192185 A1 | 12/2001 |
| WO | 2012013687 A1 | 2/2012 |
| WO | 2015128229 A1 | 9/2015 |

OTHER PUBLICATIONS

Kumaravelu Ganesan et al.; An all-diamond, hermetic electrical feedthrough array for a retinal prosthesis; Biomaterials; Jan. 2014; vol. 35, Issue 3, pp. 908-915, Abstract, Introduction, Figs 1-2.
(Continued)

*Primary Examiner* — Lindsey G Wehrheim
(74) *Attorney, Agent, or Firm* — Stevens & Showalter LLP

(57) ABSTRACT

The present disclosure provides a method of forming a hermetically sealed enclosure that comprises a diamond material. The method comprises providing first and second enclosure components comprising the diamond material and having first and second recesses, respectively, at edge por-
(Continued)

tions. At least one of the first and second enclosure components has a cavity. The enclosure components have respective contact surfaces at the first and second recesses and are shaped such that an outer channel is formed by the co-operation of the first and second recesses when the first and second enclosure components are contacted at the contact surfaces to form the enclosure. The method further comprises bonding a first type of material to at least surface portions of the first and second recesses of the first and second enclosure components, respectively. The method also comprises bonding a second type of material to the first type of material so that the second type of material covers at least portions of the first type of material. The second type of material is biocompatible and suitable for forming a hermetically sealed seal. In addition, the method comprises contacting the enclosure components to form the enclosure and bonding the second type of material of the first enclosure component to the second type of material of the second enclosure component so as to form a hermetically sealed seal in the outer channel.

19 Claims, 5 Drawing Sheets

(51) Int. Cl.
B23K 26/21 (2014.01)
B23K 26/364 (2014.01)
B23K 1/00 (2006.01)
B23K 1/19 (2006.01)
B23K 103/00 (2006.01)
A61N 1/36 (2006.01)

(52) U.S. Cl.
CPC ........ *B23K 26/364* (2015.10); *B23K 35/3006* (2013.01); *B23K 35/3013* (2013.01); *A61N 1/36046* (2013.01); *B23K 2103/50* (2018.08)

(56) References Cited

U.S. PATENT DOCUMENTS

2013/0236735 A1* 9/2013 De Wit ................ A61B 18/201
428/596
2014/0094885 A1 4/2014 Meffin et al.

OTHER PUBLICATIONS

Irina Talanina ; International Search Report; International Application No. PCT/AU2015/000646; dated Nov. 25, 2015; Australian Patent Office; Woden, ACT, Australia.
Irina Talanina ; Written Opinion of the International Searching Authority; International Application No. PCT/AU2015/000646; dated Nov. 25, 2015; Australian Patent Office; Woden, ACT, Australia.
Georgios Chalaftris; Extended European Search Report; European Patent Application No. 15653945.2; dated Jul. 4, 2017; European Patent Office; Munich, Germany.

\* cited by examiner

METHOD OF FORMING AN ENCLOSURE

FIELD OF THE INVENTION

The present invention relates to a method of forming an enclosure that is biocompatible and comprises a diamond material.

Throughout this specification the term "diamond material" is used for films or bulk materials of crystalline diamond material, poly-crystalline diamond material, nano-crystalline diamond material and also for diamond-like materials including glassy carbon and diamond-like carbon materials.

BACKGROUND OF THE INVENTION

Medical devices that include electronic components are frequently implanted into the human body. Such medical devices include cochlear implants, pacemakers, retinal prostheses and other devices. It is important that the electronic components of such medical devices are protected from fluid exposure and of critical importance that the biological tissue into which the device is implanted is only in contact with biocompatible material.

It has recently been proposed to form portions of such implantable devices from a diamond material as diamond is a biocompatible and strong material that is impermeable to fluid ingress. The present invention provides further improvement.

SUMMARY OF THE INVENTION

In accordance with a first aspect of the present invention, there is provided a method of forming an enclosure, the method comprising the steps of:
  providing first and second enclosure components comprising a diamond material and having first and second recesses, respectively, at edge portions, at least one of the first and second enclosure components having a cavity, the enclosure components having respective contact surfaces at the first and second recesses and being shaped such that an outer channel is formed by the co-operation of the first and second recesses when the first and second enclosure components are contacted at the contact surfaces to form the enclosure;
  bonding a first type of material to at least surface portions of the first and second recesses of the first and second enclosure components, respectively;
  bonding a second type of material to the first type of material so that the second type of material covers at least portions of the first type of material, the second type of material being biocompatible and suitable for forming a hermetically sealed seal;
  contacting the enclosure components to form the enclosure; and
  bonding the second type of material of the first enclosure component to the second type of material of the second enclosure component so as to form a hermetically sealed seal in the outer channel.

The first type of material that is bonded to at least a surface portion of the first recess may be the same or may be different to the first type of material that is bonded to at least a surface portion of the second recess. Further, the second type of material that is bonded to the first type of material in the first recess may be the same or may be different to the second type of material that is bonded to the first type of material in the second recess.

The first type of material may comprise a material that forms a carbide material with the diamond material of the first and second enclosure components. The first type of material may be an alloy comprising silver, titanium, niobium, nickel, chromium, molybdenum, silicon, vanadium, and/or copper.

The second type of material may also be an alloy and may comprise gold, a ceramic material such as a ceramic material having low thermal expansion, and/or another biocompatible material.

In one specific embodiment the first type of material is an alloy that comprises silver and a metal, such as titanium, that is suitable for forming a carbide material. Further, the second type of material comprises in this embodiment a gold alloy and may also comprise a metal that is suitable for forming a carbide material.

The steps of bonding the first type of material and the second type of material may comprise providing a first brazing material and a second brazing material and melting the first and second brazing material to form the first and second type of materials, respectively. The first material may comprise more than 90% silver and may further comprise titanium and/or nickel. The second material may comprise more than 90% gold and may further comprise titanium, copper and/or aluminium.

The step of bonding the second type of material of the first enclosure component to the second type of material of the second enclosure component may comprise welding, such as laser welding.

The first and second recesses may be substantially L-shaped cut outs at edges of the first and second enclosure components, respectively and may be shaped such that a substantially U-shaped channel is formed when the first and second enclosure components are contacted at the contact surfaces to form the enclosure.

The first and second recesses may entirely surround at least components of the first and second enclosure components, respectively.

The method may further comprise forming the first and second recesses in the first and second enclosure components, respectively, which may for example comprise laser milling. Forming the first and second recesses may comprise forming a trench or channel and subsequently performing a longitudinal cut through the trench or channel so that recesses, such as substantially L-shaped recesses, are formed at edges of the first and second enclosure components. Performing a longitudinal cut through the trench or channel may be performed before bonding the first and second type of materials. Alternatively, performing a longitudinal cut through the trench or channel may be performed after bonding the first and second type of materials such that the cut is performed through the first and second type of materials, which are then located directly at the edges of the first and second enclosure components.

Advantageously, the method provides a way of hermetically sealing the enclosure in a manner such that components that are within the enclosure are not heated up when the enclosure components are bonded to one another. Such a method therefore facilitates the use of heat sensitive components, for example an ASIC, within the hermetically sealed enclosure.

In accordance with a second aspect of the present invention, there is provided a biocompatible enclosure comprising:
  a first enclosure component being biocompatible and comprising a diamond material;

a second enclosure component being biocompatible and comprising a diamond material;

a first type of material arranged at edge portion of the first and second enclosure components, the first type of material comprising a material that is bonded with the diamond material;

a second type of material that is biocompatible and arranged over, and bonded to, the first type of material;

wherein the first and second type of material form a hermetically sealed seal in the outer channel and between the first and second enclosure components, and wherein the second type of material covers the first type of material whereby the formed enclosure is biocompatible.

The first type of material and the second type of material may be arranged in an outer channel formed by aligned recesses of the first and second enclosure components.

The first type of material may have formed a carbide material with diamond material. The first type of material may comprise silver, a silver alloy, and may further comprise titanium, niobium, nickel, chromium, molybdenum, silicon, vanadium and/or copper, The second type material may comprise gold, a gold alloy, and may further comprise titanium a ceramic material such as a ceramic material having low thermal expansion, and/or another biocompatible metal.

The invention will be more fully understood from the following description of specific embodiments of the invention. The description is provided with reference to the accompanying drawings.

BRIEF DESCRIPTION OF DRAWINGS

FIG. 3 is a cross sectional view of the enclosure component of FIG. 2 wherein a channel of the enclosure component has been cut through;

DETAILED DESCRIPTION OF DRAWINGS

Figure 1:
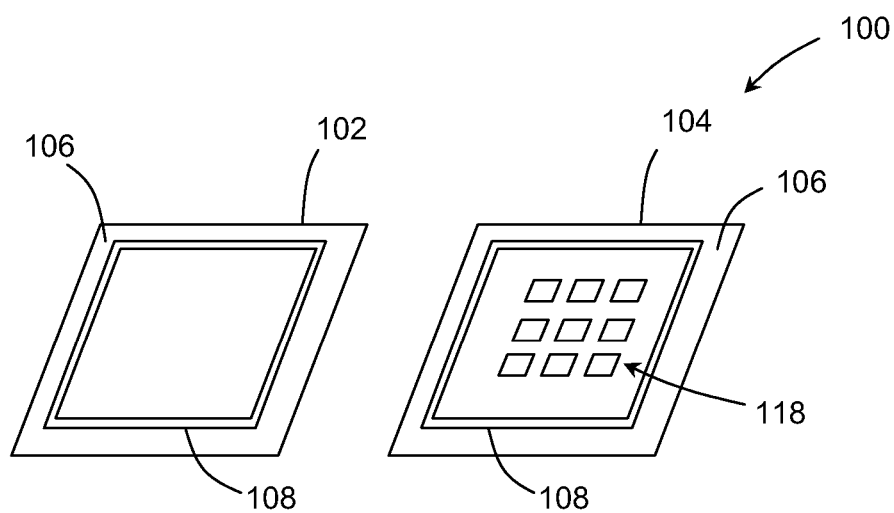
FIG. 1 is a view of enclosure components for an enclosure in accordance with an embodiment of the present invention.

Embodiments of the present invention relate to bonding first and second enclosure components to each other to form a hermetically sealed enclosure that is biocompatible. The first and second enclosure components comprise, or are formed from, a diamond material. The hermetically sealed enclosure can house electronic components and be provided in the form of a medical device, for example as a retinal implant.

Although diamond is biocompatible and is biochemically stable, it presents some difficulties when used for a hermetically sealed enclosure as it is non-ductile and therefore cannot be welded; this presents difficulties for closing a diamond-based enclosure and sealing it hermetically.

Embodiments of the present invention melt a first brazing material, for example a silver-based brazing material which can wet with the diamond material, to form a first material at edge portions of the first and second enclosure components and melt a second brazing material, such as gold-based brazing alloy which can wet with the formed first material, to form the second material over the first material. The second material is formed such that it covers the first material and the first and second enclosure components are then welded together at the second material whereby a hermetically sealed enclosure is formed that is biocompatible. A specific example is described in more detail below with reference to FIGS. 1 to 4.

Referring to FIGS. 1 to 4, a hermetically sealed enclosure 100 comprises a first enclosure component 102 and a second enclosure component 104. In this example, each of the first and second enclosure components 102, 104 are formed from a diamond material 106 and are biocompatible. The enclosure component 102 is a lid portion and the enclosure component 104 has a cavity for receiving electronic components. The enclosure 100, when equipped with the electronic components and hermetically sealed, is used as a retinal implant. It will be appreciated that the hermetically sealed enclosure 100 could be used for any appropriate purpose where it is desired to provide a biocompatible hermetically sealed enclosure.

The first and second enclosure components 102, 104 each comprise an encircling channel 108 that has been formed in the diamond material 106. Each channel 108 comprises a first material 110 that is bonded with the diamond material 106. In this specific example the first material 110 is formed from a silver brazing alloy (silver 92.75%, copper 5%, titanium 1.25%, aluminium 1%) and forms a carbide material with the diamond material of the enclosure components 102 and 104. The first material 110 is arranged adjacent and within the channel 108. Each enclosure component 102, 104 also comprises a second material 112, the second material 112 comprising a material that is biocompatible, can form a hermetically sealed seal, and can wet with the first material 110. In this specific example, the second material 112 is formed from a gold brazing alloy (gold 96.4%, nickel 3%, titanium 0.6%). The second material 112 is arranged over and covers a respective first material 110.

Figure 2:
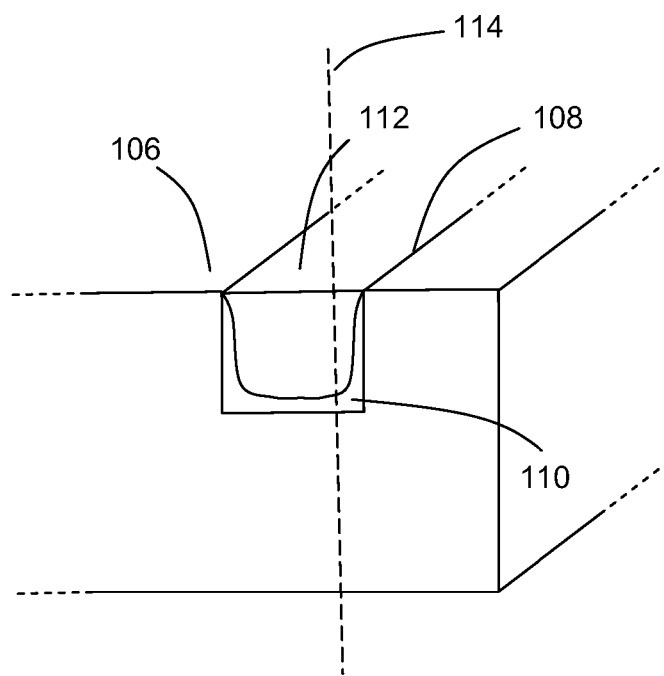
FIG. 2 is a cross sectional view of a portion of one of the enclosure components of FIG. 1 showing a channel thereof.
Figure 3:
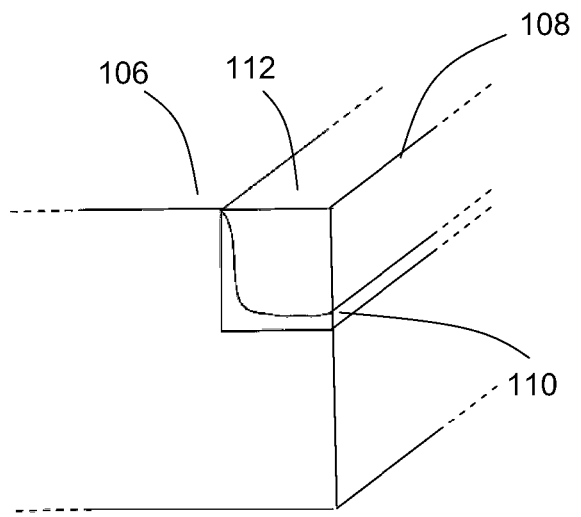

In FIG. 1, the hermetically sealed enclosure 100 is shown unassembled. When forming the hermetically sealed enclosure 100, a longitudinal cut is performed through the channel 108 of each of the enclosure components 102, 104, for example using laser cutting or another appropriate cutting technique, such that the second material 112 is exposed at an edge of each of the enclosure components 102, 104. In this example, the channel 108 shown in FIG. 2 is cut along the dashed line 114, resulting in the formation shown in FIG. 3.

The first and second enclosure components 102, 104 are then arranged adjacent one another such that each channel 108, and in particular the second material 112 contained within each channel 108, is aligned. The second material 112 is then heated, for example by using a laser welder, such that the second material 112 of the first enclosure component 102 bonds with the second material 112 of the second enclosure component 104 so as to form a hermetically sealed seal between the first and second enclosure components 102, 104. As the second material 112 covers the first material, it is avoided that the first material is exposed and the formed hermetically sealed enclosure is biocompatible.

Although in this example the first material 110 is formed using a silver brazing alloy and the second material 112 is formed using a gold brazing alloy, it will be appreciated that the first material 110 may be any appropriate material that can form a carbide material with the diamond material 106, and that can wet with the second material 112. For example, the first material 110 may comprise titanium, niobium, nickel, chromium, molybdenum, silicon or vanadium. The first material may further comprise a material that facilitates spreading on the diamond material 106, but does not react with the diamond material, for example copper or silver. It will also be appreciated by a person skilled in the art that the second material 112 may comprise any appropriate material that can wet with the first material 110, is biocompatible, and can form a hermetic seal. For example, the second material 112 may be a ceramic material such as a ceramic material having low thermal expansion, or another biocompatible metal.

Figure 4:
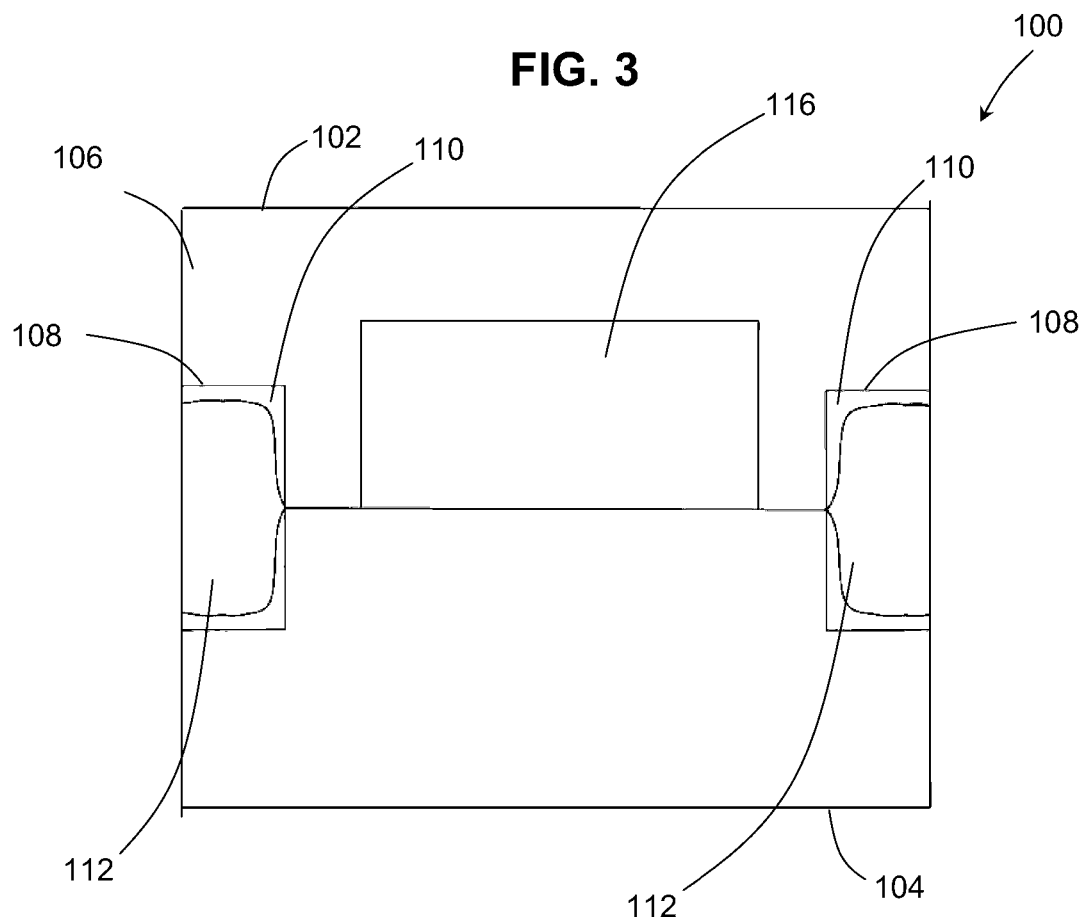
FIG. 4 is a cross sectional view of a hermetically sealed enclosure formed using the enclosure components shown in FIG. 3.

The hermetically sealed enclosure 100 is shown in its formed configuration in FIG. 4, whereby the first and second enclosure components 102, 104 have been arranged such that the second materials 112 of the respective enclosure components 102, 104 are aligned and bonded. The cross sectional view of FIG. 4 also shows a cavity 116 in which components, such as an application-specific integrated circuits (ASIC), can be arranged. In this example, a region of the first enclosure component 102 that corresponds to the formed cavity 116 is removed by laser milling prior to the enclosure components 102, 104 being bonded to one another.

Figure 5:
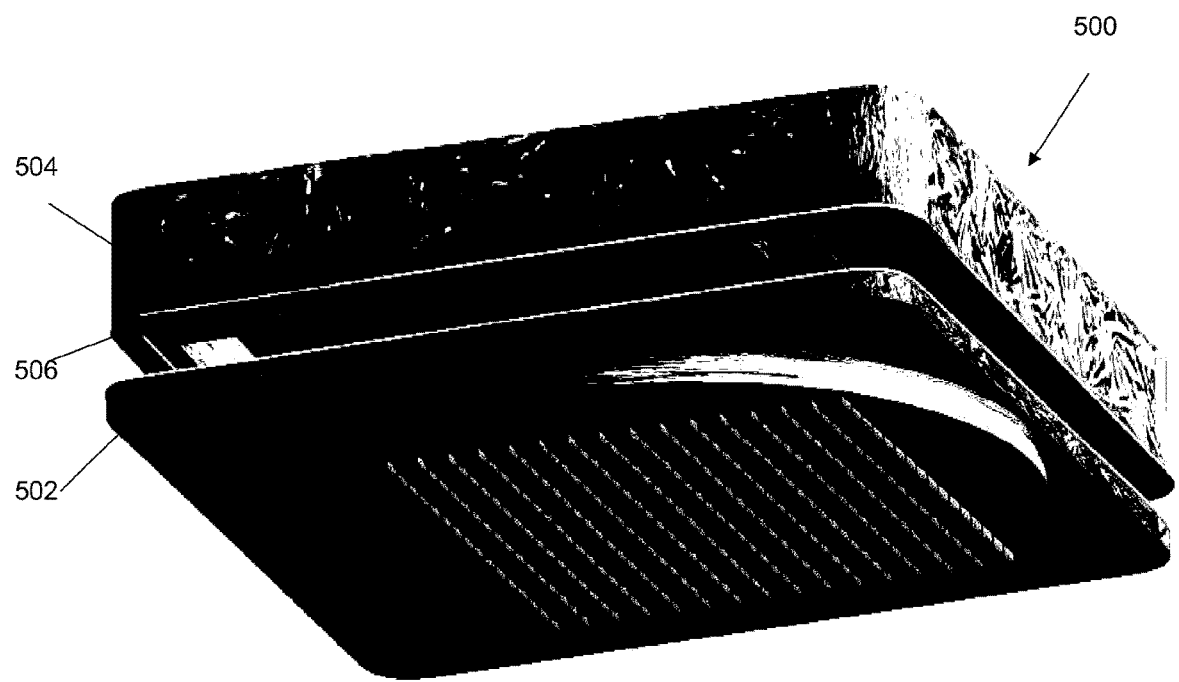
FIG. 5 shows enclosure components formed in accordance with an embodiment of the present invention.

Referring now to FIGS. 5-8 the fabrication of a biocompatible and hermetically sealed enclosure is described. FIG. 5 shows an enclosure 500 before assembly. The enclosure 500 comprises enclosure components 502 and 504. Visible is also a second material 506 at edge portions and within recesses of the enclosure components 504 and 502. The second material 506 covers a first material (not shown) and the first material and the second material 506 correspond to the above-described first material 110 and the second material 112, respectively.

Figure 6:
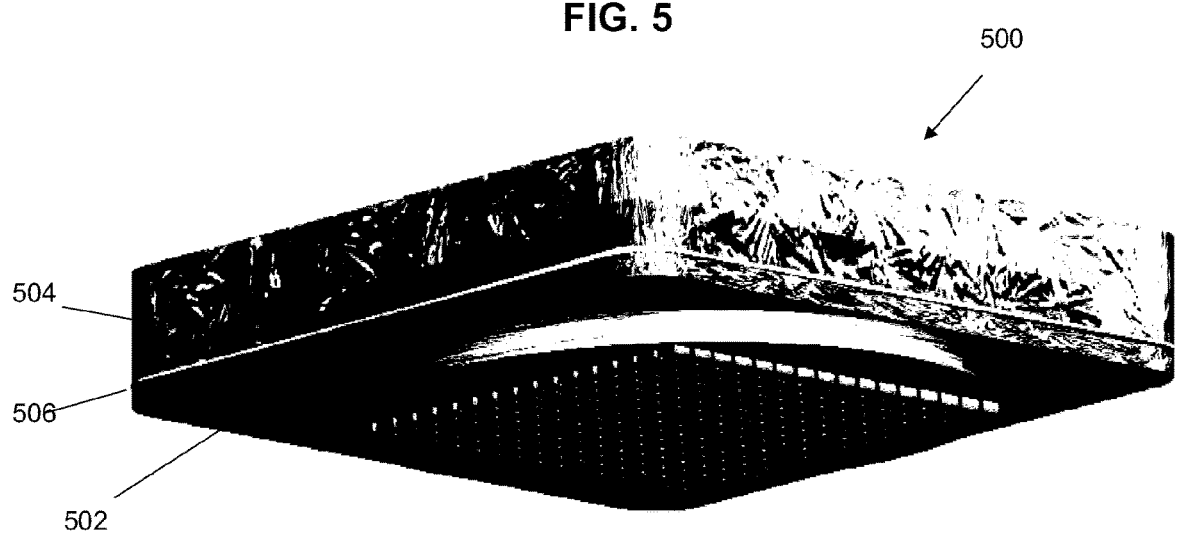
FIG. 6 shows the enclosure formed from the enclosure components shown in FIG. 5.

FIG. 6 shows the assembled and hermetically sealed enclosure 500. The enclosure components 502 and 504 were welded together at the second material 506 by heating the second material 506 using a laser.

Figure 7:
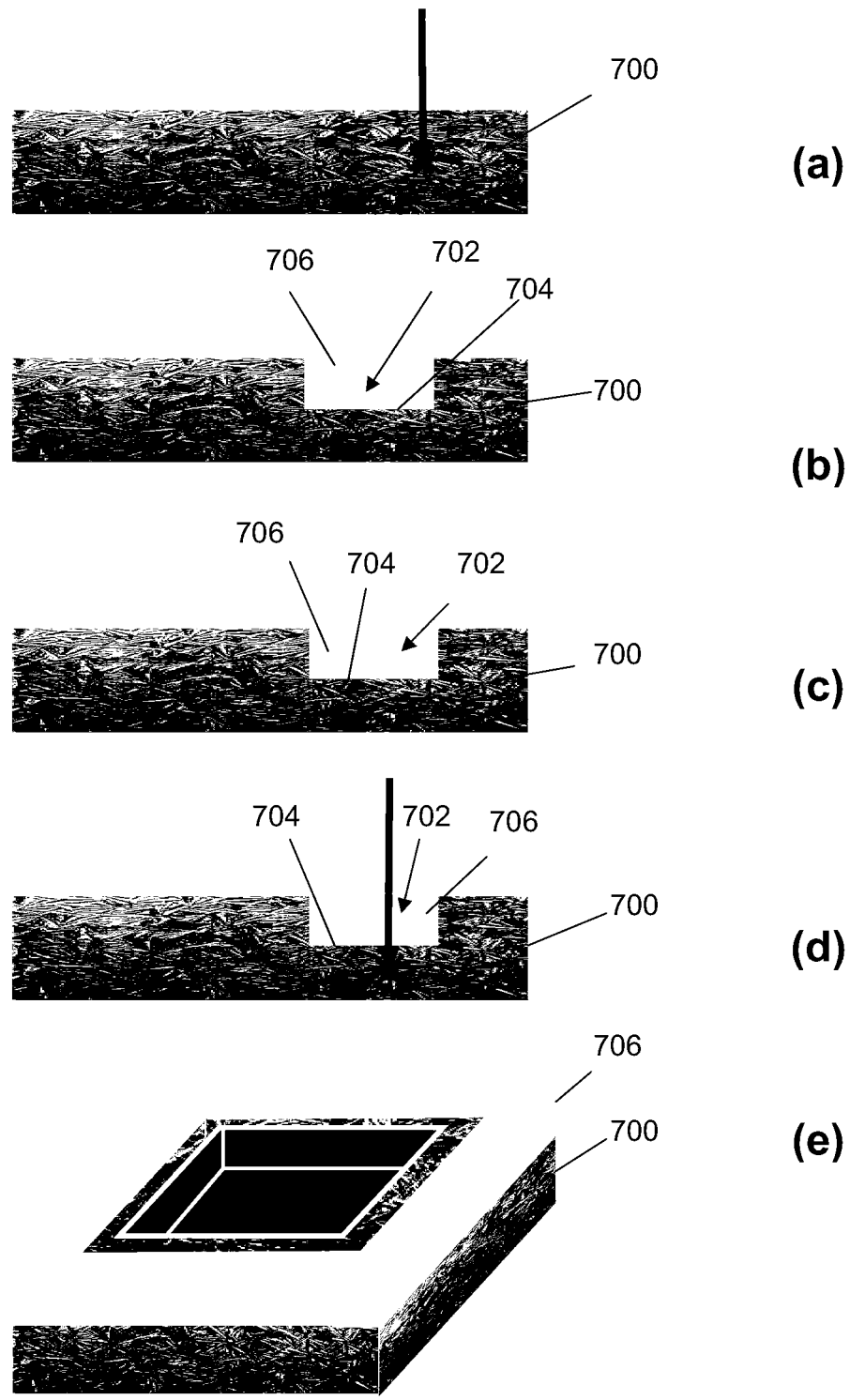
FIG. 7 illustrates processing steps of forming the hermetically sealed enclosure in accordance with an embodiment of the present invention.
Figure 8:
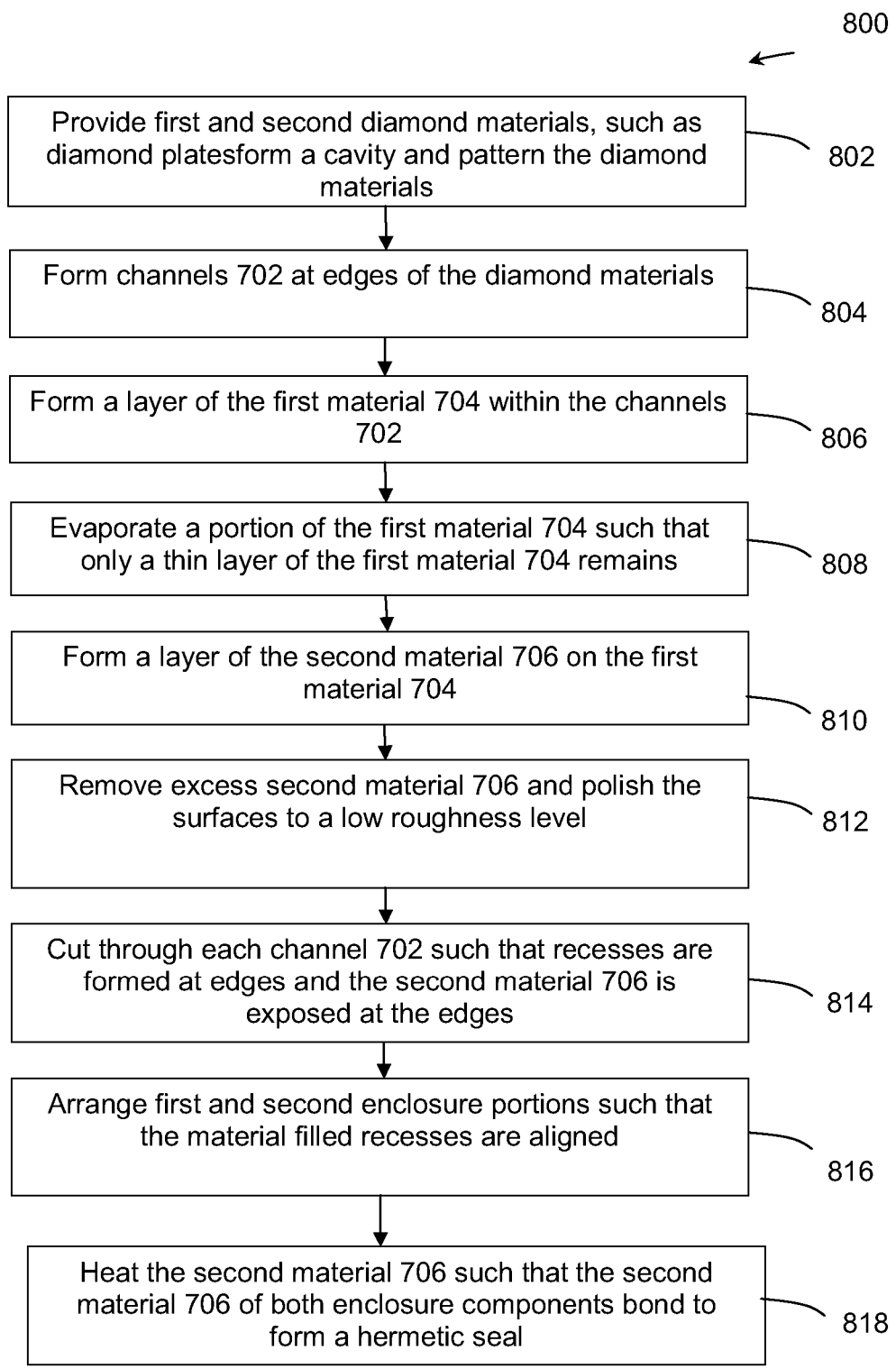
FIG. 8 is a flow chart of a method of forming the hermetically sealed enclosure in accordance with an embodiment of the present invention.

FIG. 7 schematically illustrates processing steps of a method of forming the enclosure and FIG. 8 is a corresponding flow chart. For forming the enclosure 500 components 502, 504 two polycrystalline diamond (PCD) plates 700, either 0.25 or 0.5 mm in thickness, are provided (step 802; FIG. 7(a) only shows one diamond plate 700). The diamond plates 700 are patterned and a cavity is excavated using a 2.5 W Nd:YAG, 532 nm wavelength, nanosecond pulsed laser micromachining system.

In step 804, the channels 702 are formed at edge portions of the diamond plates 700 using the above-mentioned laser micromachining system. In this example, the channels are formed such that the cross-sectional area of the channels is 50×50 μm². Graphite debris, formed during laser milling or cutting, is removed by etching in a hydrogen plasma or by boiling in a mixture of $NaNO_3/H_2SO_4$ (conc. 1 mg/mL).

Step 806 forms a layer of a first material 704 within the channels 702. The first material 704 is formed by melting a silver brazing material (Ag 92.75%, Cu 5%, Al 1%, Ti 1.25%) over the PCD surface on a resistively-heated element under vacuum of at least $10^{-5}$ mbar. After melting and spreading of the silver brazing material at a temperature of approximately ~950° C., the temperature was raised to ~1000° C. and held to evaporate excess silver brazing material (step 808). The evaporation rate of the silver brazing material was monitored with a quartz crystal monitor. The temperature was reduced slowly once the evaporation rate dropped to near zero. The resulting thickness of the adhesion layer formed from the silver brazing material is between 1 and 10 microns.

In a further step 810, a layer of a second material 706 is then formed over the first material 704. A gold-brazing material (Au 96.4%, Ni 3%, Ti 0.6%) is brazed over the first material 704 in a vacuum (10 minutes, 1000° C.). Step 812 removes excess gold brazing material by mechanical polishing.

Step 814 performs longitudinal laser cuts through the channels (FIG. 7(d)) such that the second material 706 is exposed in recesses at edges.

Step 816 aligns two enclosure components 700 such that the second materials 706 of each enclosure component are in direct contact. In this example the second materials 706 are then welded together using a 5 W Nd:YAG, 1064 nm wavelength, microsecond pulsed laser welder with 10 μm tolerance. The laser welding is conducted through a glass window in the top of a welding chamber. The chamber is fitted with vacuum and gas inlet lines, to control the atmosphere within the chamber and with a hermetic stepper motor to rotate the sample during welding. The formed seal is hermetic and the formed enclosure biocompatible, as will also be discussed further below.

It will be appreciated that the hermetically sealed enclosure 500 may be formed using different materials. For example, the enclosure components may additionally comprise a material other than a diamond material. Further, it will be appreciated that only one of the enclosure components may comprise the second material. For example, the first enclosure component may be formed as described above, but the second enclosure component may only comprise the first material such that, when the enclosure components are arranged adjacent one another and the second material 112 is heated, the second material 112 can bond with the first material 110 within the channel 108 of the second enclosure component 104 to effect closure of the hermetically sealed enclosure 100.

The following will discuss ageing and hermetically testing of enclosures formed using the method as described above with reference to FIGS. 5 to 8. A hermetically sealed diamond enclosure formed as described above was aged at 80° C. in 0.13 M sterile NaCl for 24 days. The real time equivalent is approximately 16 months calculated using the Arrhenius methods outlined in International Standard, ISO-11607 (Packaging for terminally sterilized medical devices). The calculation assumes a reaction rate factor ($Q_{10}$) of 2 and ambient (implanted) temperature of 37° C. The hermetically sealed diamond enclosure was visually inspected before and after the aging process using scanning electron microscopy. No differences could be observed between the before- and after-ageing images. Small sharp edges produced during laser cutting or polishing of the brazing material were unaffected by the ageing process and existing height difference between the diamond surface and the adjacent the brazing material did not change.

The following will consider the biocompability and histocompatibility of the second material (Au 96.4%, Ni 3%, Ti 0.6%). Samples were implanted into the back muscle of Guinea pigs for a period of either 12 or 15 weeks. Following histopathological processing of the implantation sites, the histocompatibility of the second material was assessed relative to medical grade silicone and PCD as negative controls and a piece of diamond treated with a stannous octoate solution (a metal complex known to cause a strong histopathological response) as a positive control. The relative histocompatibility was established by comparing the thickness of the gliotic capsule covering the face of the implants and by analysis of the tissue adjacent to the diamond by a specialist pathologist. The pathologist scored each section from 0 (no response) to 4 (severe response) in the three categories; acute, chronic and foreign body response based on the identifiable cell types present. The pathologist scores for the collated gold-based brazing material were (1.2±0.2) indicating no evidence of acute response, low chronic response and no foreign body response.

The fibrotic encapsulation over the second material was thin and comparable to the control materials employed (medical grade silicone and PCD). The implanted second material samples were closely examined before and after implantation. Minute topographical features in the second material samples formed during the polishing process were unchanged over the 15 weeks. The size shape and sharpness of small features did not change during the 15 week period indicating excellent biostability of the second material.

The invention claimed is:

1. A method comprising the steps of:
providing first and second enclosure components comprising a diamond material and having first and second recesses, respectively, at edge portions, at least one of the first and second enclosure components having a cavity, the enclosure components having respective contact surfaces at the first and second recesses and being shaped such that an outer channel is formed by the co-operation of the first and second recesses when the first and second enclosure components are contacted at the contact surfaces to form the enclosure;
bonding a first type of material to at least surface portions of the first and second recesses of the first and second enclosure components, respectively;
bonding a second type of material to the first type of material so that the second type of material covers the first type of material, the second type of material being biocompatible and suitable for forming a hermetically sealed seal;
contacting the enclosure components to form the enclosure; and
bonding the second type of material of the first enclosure component to the second type of material of the second enclosure component by laser welding so as to form a hermetically sealed seal in the outer channel.

2. The method of claim 1 wherein the first type of material comprises a material that forms a carbide material with the diamond material of the first and second enclosure components.

3. The method of claim 1 wherein the first type of material comprises silver or molybdenum.

4. The method of claim 1 wherein the second type of material comprises gold.

5. The method of claim 1 wherein the first type of material is an alloy that comprises silver and a metal that forms a carbide material with the diamond material and wherein the second type of material comprises a gold alloy.

6. The method of claim 1 wherein the steps of bonding the first type of material and the second type of material comprise providing a first brazing material and a second brazing material and melting the first and second brazing material to form the first and second type of materials, respectively.

7. The method of claim 6 wherein the first brazing material comprises more than 90% silver and wherein the second brazing material comprises more than 90% gold.

8. The method of claim 1 wherein the first and second recesses are substantially L-shaped cut outs at edges of the first and second enclosure components, respectively, and are shaped such that a substantially U-shaped channel is formed when the first and second enclosure components are contacted at the contact surfaces to form the enclosure.

9. The method of claim 1 wherein the first and second recesses entirely surround at least components of the first and second enclosure components, respectively.

10. The method of claim 1 further comprising forming the first and second recesses in the first and second enclosure components, respectively.

11. The method of claim 10 wherein forming the first and second recesses comprises forming a trench or channel and subsequently performing a longitudinal cut through the trench or channel so that recesses are formed at edges of the first and second enclosure components.

12. The method of claim 11 wherein performing a longitudinal cut through the trench or channel is performed after bonding the first and second type of materials such that the cut is performed through the first and second type of materials, which are then located directly at the edges of the first and second enclosure components.

13. A biocompatible enclosure comprising:
a first enclosure component being biocompatible and comprising a diamond material;
a second enclosure component being biocompatible and comprising a diamond material;
a first type of material arranged at edge portions of both the first and second enclosure components, the first type of material comprising a material that is bonded with the diamond material;
a second type of material that is biocompatible and arranged over, and bonded to, the first type of material;
the first and second enclosures each having a contact surface that contact one another to define an outer channel at the edge portions of the first and second enclosures;
wherein the first and second type of material form a hermetically sealed seal in the outer channel and between the first and second enclosure components, and wherein the second type of material covers the first type of material whereby the formed enclosure is biocompatible.

14. The biocompatible enclosure of claim 13 wherein the first type of material and the second type of material are arranged in the outer channel that is formed by aligned recesses of the first and second enclosure components.

15. The biocompatible enclosure of claim 13 wherein the first type of material has formed a carbide material with the diamond material.

16. The biocompatible enclosure of claim 13 wherein the first type of material comprises a silver alloy or molybdenum.

17. The biocompatible enclosure of claim 13 wherein the second type of material comprises a gold alloy.

18. The biocompatible enclosure of claim 13, wherein the second type of material is formed by laser welding.

19. A method comprising the steps of:
providing first and second enclosure components comprising a diamond material and having first and second recesses, respectively, at edge portions, at least one of the first and second enclosure components having a cavity, the enclosure components having respective contact surfaces at the first and second recesses and being shaped such that an outer channel is formed by the co-operation of the first and second recesses when the first and second enclosure components are contacted at the contact surfaces to form the enclosure;

bonding a first type of material to at least surface portions of the first and second recesses of the first and second enclosure components, respectively;

bonding a second type of material to the first type of material so that the second type of material covers at least portions of the first type of material, the second type of material being biocompatible and suitable for forming a hermetically sealed seal;

contacting the enclosure components to form the enclosure;

bonding the second type of material of the first enclosure component to the second type of material of the second enclosure component so as to form a hermetically sealed seal in the outer channel, and forming the first and second recesses in the first and second enclosure components, respectively, wherein forming the first and second recesses comprises forming a trench or channel and subsequently performing a longitudinal cut through the trench or channel so that recesses are formed at edges of the first and second enclosure components.

* * * * *